(12) United States Patent
Kontermann et al.

(10) Patent No.: US 6,759,518 B1
(45) Date of Patent: Jul. 6, 2004

(54) SINGLE-CHAIN MULTIPLE ANTIGEN-BINDING MOLECULE, ITS PREPARATION AND USE

(75) Inventors: Roland Kontermann, Ebsdorfergrund (DE); Hans-Harald Sedlacek, Marburg (DE); Rolf Mueller, Marburg (DE)

(73) Assignee: Vectron Therapeutics AG (DE)

( * ) Notice: Subject to any disclaimer, the term of this patent is extended or adjusted under 35 U.S.C. 154(b) by 0 days.

(21) Appl. No.: 09/288,719

(22) Filed: Apr. 9, 1999

(30) Foreign Application Priority Data

| Apr. 9, 1998 | (DE) | 198 16 141 |
| Jun. 18, 1998 | (DE) | 198 27 239 |

(51) Int. Cl.$^7$ .................. C07K 16/00; C12P 21/08; A61K 48/00; C12N 15/63
(52) U.S. Cl. .................. 530/387.3; 530/387.7; 435/320.1; 536/23.1; 514/2; 514/44
(58) Field of Search .................. 435/320.1; 530/387.3, 530/387.7; 536/23.1; 514/2, 44

(56) References Cited

U.S. PATENT DOCUMENTS

| 5,830,880 A | 11/1998 | Sedlacek et al. | 514/44 |
| 5,854,019 A | 12/1998 | Sedlacek et al. | 435/69.1 |
| 5,885,833 A | 3/1999 | Mueller et al. | 435/372 |
| 5,916,803 A | 6/1999 | Sedlacek et al. | 435/320.1 |

FOREIGN PATENT DOCUMENTS

| DE | 196 17 851 | 11/1997 |
| DE | 196 39 103 | 3/1998 |
| DE | 197 04 301 | 3/1998 |
| DE | 196 49 645 | 4/1998 |
| DE | 196 51 443 | 6/1998 |
| DE | 197 10 643 | 9/1998 |
| EP | 0 790 313 | 8/1997 |
| EP | 0 860 445 | 8/1998 |
| WO | 93/06217 | 4/1993 |
| WO | 96/06943 | 3/1996 |

OTHER PUBLICATIONS

M. Deonarain; Ligand–targeted receptor–mediated vectors for gene delivery; 1998, Exp. Opin. Ther. Patents 8(1): 53–69.*

N. Miller et.al.; Target d vectors for gene therapy; 1995, FASEB Journal 9,190–199.*

Shi–Zhen Hu et al. "Minibody: A Novel Engineered Anti-Carcinoembryonic Antigen Antibody Fragment (Single–Chain Fv–$C_H3$) Which Exhibits Rapid, High–Level Targeting of Xenografts" Cancer Research 56: 3055–3061 (Jul. 1, 1961).

Plückthun et al.; "New Protein Engineering Approaches to Multivalent and Bispecific Antibody Fragments"; Immunotechnology; vol. 3; 1997; pp. 83–105.

Fitzgerald et al.; "Improved Tumour Targeting by Disulphide Stabilized Diabodies Expressed in *Pichia pastoris*"; Protein Engineering; vol. 10, No. 10; 1997; pp. 1221–1225.

Hayden et al.; "Single–chain Mono– and Bispecific Antibody Derivatives With Novel Biological Properties and Antitumor Activity From a COS Cell Transient Expression System"; Therapeutic Immunology; vol. 1; 1994; pp. 3–15.

Kontermann et al.; "Enzyme Immunoassays Using Bispecific Diabodies"; Immunotechnology; vol. 3; 1997; pp. 137–144.

Mullen; "Metabolic Suicide Genes in Gene Therapy"; Pergamon; vol. 63; 1994; pp. 199–207.

Power et al., "High–Level Temperature–Induced Synthesis Of An Antibody VH–Domain in *Escherichia coli* Using The PelB Secretion Signal", *Gene*, vol. 113:95–99, (1992).

Renner et al., "Cure Of Xenografted Human Tumors By Bispecific Monoclonal Antibodies And Human T Cells", *Science*, vol. 264:833–835, (1994).

Riechmann et al., "Reshaping Human Antibodies For Therapy", *Nature*, 332:323–327, (1988).

Rosen et al., "The Location Of Cis–Acting Regulatory Sequences In The Human T Cell Lymphotropic Virus Type III (HTLV–III/LAV) Long Terminal Repeat", *Cell*, vol. 41:813–823, (1985).

Sahin et al., "Specific Activation Of The Prodrug Mitomycin Phosphate By A Bispecific Anti–CD30/Anti–Alkaline Phosphatase Monoclonal Antibody", *Cancer Research*, vol. 50:6944–6948, (1990).

Van De Winkel et al., "Immunotherapeutic Potential Of Bispecific Antibodies".

Verhoeyen et al., "Reshaping Human Antibodies: Grafting An Antilysozyme Activity", *Science*, vol. 239:1534–1537, (1988).

Westerink et al., "Anti–idiotypic Antibodies As Vaccines Against Carbohydrate Antigens", *Springer Semin Immunopathol*, vol. 15:227–234, (1993).

Zhu et al., "Remodeling Domain Interfaces To Enhance Heterodimer Formation", *Protein Science*, vol. 6:781–788, (1997).

McCartney et al., "Engineering Disulfied–linked Single–chain Fv Dimers (sFv')$_2$ Made By Protein Folding And Bonded Through C–terminal Cysteinyl Peptides", *Protein Engineering*, vol. 8(3):301–314, (1994).

(List continued on next page.)

*Primary Examiner*—Anne Marie S. Wehbé
(74) *Attorney, Agent, or Firm*—Saliwanchik, Lloyd & Saliwanchik

(57) ABSTRACT

The present invention relates to a single-chain, multiple antigen-binding molecule with diverse variable domains of a heavy and of a light chain of an immunoglobulin, which are connected in the form of a VH-VL construct, which are in turn connected together via a peptide, and to the preparation and use thereof as pharmaceutical or diagnostic aid.

19 Claims, 5 Drawing Sheets

OTHER PUBLICATIONS

Hochuli et al., "Genetic Approach To Facilitate Purification Of Recombinant Proteins With A Novel Metal Chelate Absorbent", *Biotechnology*, pp. 1321–1325, (1988).

Holliger et al., "Engineering Bispecific Antibodies", *Current Opinion in Biotechnology*, vol. 4:446–449, (1993).

Holliger et al., Retargeting Serum Immunoglobulin With Bispecific Diabodies, *Nature Biotechnology*, vol. 15:632–636, (1997).

Holliger et al., "Diabodies: Small Bivalent And Bispecific Antibody Fragments", *Proc. Natl. Acad. Sci. U.S.A.*, vol. 90:6444–6448, (1993.

Jones et al., "Replacing The Complementary–Determining Regions In A Human Antibody With Those From A Mouse", *Nature*, vol. 321:523–525, (1986).

Kontermann et al., "Complement Recruitment Using Bispecific Diabodies", *Nature Biotechnology*, vol. 15, (1997).

Krebs et al., "Recombinant Human Single Chain Fv Antibodies Recognizing Human Interleukin–6", *The Journal of Biological Chemistry*, pp. 2858–2865, (1998).

Lucibello et al., "Periodic cdc25C Transcription Is Mediated By A Novel Cell Cycle–Regulated Repressor Element (CDE)", *The EMBO Journal*, vol. 14(1):132–142, (1995).

Mallender et al., "Construction, Expression, And Activity Of A Bivalent Bispecific Single–Chain Antibody", *The Journal Of Biological Chemistry*, vol. 269(1): 199–206, (1994).

Milstein et al., "Hybrid Hybridomas And Their Use in Immunohistochemistry", *Nature*, vol. 305(6):537–541, (1983).

Munro et al., Ann Hsp70–like Protein In The ER: Identity With The 78 kd Glucose–Regulated Protein And Immunoglobulin Heavy Chain Binding Protein, *Cell*, vol. 46:291–300, (1986).

Nisonoff et al., "Quantitative Estimation Of The Hybridization Of Rabbit Antibodies", *Nature*, vol. 194:355–359, (1962).

Perisic et al., "Crystal Structure Of A Diabody, A Bivalent Antibody Fragment", *Structure*, vol. 2(12):1217–1226, (1994).

Biocca et al., "Intracellular Immunization: Antibody Targeting To Subcellular Compartments", *Trends In Cell Biology*, vol. 5:248–253, (1995).

Deonarain et al., "Targeting Enzymes For Cancer Therapy: Old Enzymes in New Roles", *Br. J. Cancer*, vol. 70:786–794, (1994).

Ellis, "Vaccine Development: Progression From Target Antigen To Product", *Genetically Engineered Vaccines*, pp. 263–271, (1992).

Fanger et al., "Bispecific Antibodies", *Critical Review In Immunology*, vol. 12(3,4):101–124, (1992).

Glockshuber et al., "A Comparison Of Strategies To Stabilized Immunoglobulin $F_v$–Fragments", *Biochemistry*, vol. 29:1362–1367, (1990).

Harris et al., "Gene Therapy for Cancer Using Tumour–Specific prodrug Activation", *Gene Therapy*, vol. 1:170–175, (1994).

Hawkins et al., "A Genetic Approach To Idiotypic Vaccination", *Journal Of Immunotherapy*, vol. 14:273–278, (1993).

K. FitzGerald et al., "Improved tumour targeting by disulphide stabilized diabodies expressed in *Pichia pastoris*", Protein Engin. vol. 10, No. 10, pp. 1221–1225, 1997.

P. Holliger et al., "Specific killing of lymphoma cells by cytotoxic T–cells mediated by a bispecific diabody", Protein Engin. vol. 9, No. 3, pp. 299–305, 1996.

A. Plückthun et al., "New protein engineering approaches to multivalent and bispecific antibody fragments", Immuno. vol. 3, pp. 83–105, 1997.

Z. Zhu et al., "High level secretion of a humanized bispecific diabody from *Escherichia coli*", Biotech. vol. 14, pp. 192–196, 196.

Baltazar Becerril et al., "Toward Selection of Internalizing Antibodies from Phage Libraries", Biochemical and Biophysical Research Communications, 1999, pp. 386–393, No. 255, Academic Press.

John de Kruif et al., "Selection And Application Of Human Single Chain Fv Antibody Fragments From A Semi–synthetic Phage Antibody Display Library With Designed CDR3 Regions", J. Mol. Biol., 1995, pp. 97–105, No. 248, Academic Press Limited.

Joanne T. Douglas et al., "Targeted Gene Delivery By Tropism–Modified Adenoviral Vectors", Nature Biotechnology, Nov. 1996, pp. 1574–1578, vol. 14.

Stefan Dübel et al., "Isolation of IgG Antibody Fv–DNA From Various Mouse and Rat Hybridoma Cell Lines Using The Polymerase Chain Reaction With A Simple Set Of Primers", Journal of Immunological Methods, 1994, pp. 89–95, No. 175, Elsevier Science B.V.

S. Gottschalk et al., "A Novel DNA–Peptide Complex For Efficient Gene Transfer And Expression In Mammalian Cells", Gene Therapy, 1996, pp. 448–457, No. 3, Stockton Press.

Y.–J. Jang et al., "The Structural Basis For DNA Binding By An Anti–DNA Autoantibody", Molecular Immunology, 1998, pp. 1207–1217, No. 35, Elsevier Science Ltd.

Gabor Klivenyi et al., "Gallium–68 Chelate Imaging Of Human Colon Carcinoma Xenografts Pretargeted With Bispecific Anti–CD44$_{v6}$/Anti–Gallium Chelate Antibodies", J. Nucl Med, 1998, pp. 1769–1776, No. 39.

Anke Krebber et al., "Reliable Cloning Of Functional Antibody Variable Domains From Hybridomas and Spleen Cell Repertoires Employing A Reengineered Phage Display System", Journal of Immunological Methods, 1997, pp. 35–55, No. 201, Elsevier Science B.V.

Jayne Lesley et al., "Modulation Of Transferrin Receptor Expression And Function By Anti–Transfeerin Receptor Antibodies And Antibody Fragments", Experimental Cell Research, 1989, pp. 215–233, No. 182, Academic Press, Inc.

Dirk M. Nettelbeck et al., "Targeting Of Adenovirus To Endothelial Cells By A Bispecific Single–Chain Diabody Directed Against The Adenovirus Fiber Knob Domain And Human Endoglin (CD105)", Molecular Therapy, Jun. 2001, pp. 882–891, vol. 3, No. 6, The American Society of Gene Therapy.

He Liu et al., "Constitutive And Antibody–Induced Internalization Of Prostate–Specific Membrane Antigen", Cancer Research, Sep. 15, 1998, No. 4055–4060, No. 58.

* cited by examiner

SINGLE-CHAIN MULTIPLE ANTIGEN-BINDING MOLECULE, ITS PREPARATION AND USE

FIELD OF THE INVENTION

The present invention relates to a single-chain multiple antigen-binding molecule ("ScMAB") with diverse variable domains of a heavy and of a light chain of an immunoglobulin, which are connected in the form of a VH-VL construct, which are in turn connected together via a peptide; to nucleic acid molecules encoding ScMAB; to a vector comprising the nucleic acid molecule; to cells comprising the vector; and to the preparation and use thereof in pharmaceuticals or diagnostics.

BACKGROUND OF THE INVENTION

Bispecific antibodies which recognize two different antigens, for example a tumor cell surface antigen and an effector molecule, are widely used in experimental immunotherapy (Fanger et al., Crit. Rev. Immunol. 12, 101–124 (1992); van de Winkel et al., Immunol. Today 18, 562–564 (1997)). The effector functions recruited by bispecific antibodies include those which occur naturally in the body, such as, cytotoxic and phagocytic cells, complement components, cytokines and thrombolytic and fibrinolytic enzymes, as well as exogenous effector molecules such as, toxins, prodrug-converting enzymes and radionuclides. Thus, for example, injection of bispecific antibodies against Hodgkin's tumor-associated antigen CD30 and the T-cell antigens CD3 and CD28 in xenotransplanted tumors leads to recruitment and stimulation of cytotoxic T cells and to induction of a tumoricidal activity (Renner et al., Science 264, 833, 1994). In another approach, a bispecific antibody against CD30 and alkaline phosphatase was used to recruit the enzyme to the tumor site and thus to convert the nontoxic precursor of a drug into a toxic drug (Sahin et al., Cancer Res. 50, 6944–6948, 1990).

An alternative to injection of the purified bispecific antibody is expression and secretion of these bispecific antibodies by cells transfected in vitro or in vivo. The advantage of this strategy is that production of the bispecific antibody by the transduced cells takes place in vivo and thus there is no need for elaborate production and purification of the bispecific antibody before injection. In addition, it is possible by choosing suitable expression systems to control the expression of the bispecific antibody locally, in organs or a tumor or else systemically.

Bispecific antibodies can be prepared, for example, by chemical crosslinking (Nisonoff et al., Nature 194, 355, 1962). There are, however, a number of drawbacks associated with this approach. Upon chemical crosslinking of monoclonal or polyclonal antibody molecules of animal origin there may be inactivation of no small proportion. In addition, both hetero- and homodimers are produced. Homodimers must be separated from the required heterodimers by elaborate processes. Hybridoma cells which produce bispecific antibodies, called hybrid hybridomas, can be prepared only in a relatively elaborate way because it is necessary to fuse together two different hybridomas (Milstein et al., Nature 305, 537, 1983). The proportion of functional heterodimers is relatively low, theoretically only 10%, because the heavy and light chains of the two antibody molecules can associate with one another in any of a large number of ways. Furthermore, the starting material used mainly comprises murine monoclonal antibodies which, in turn, are immunogenic for humans.

Various bivalent or bispecific antibody molecules can also be prepared recombinantly and expressed in bacteria or eukaryotic cells (WO 93/06217). It is common to all recombinant antibody molecules that both murine and human starting molecules can be used to prepare them. Various methods have been developed to allow bispecific recombinant antibody molecules to be prepared as efficiently as possible. Various groups of molecules can be prepared using these methods.

In one group of molecules, the variable parts of the antibodies are fused to constant immunoglobulin domains (Fc, CH3, CL), in order to achieve dimerization (Hu et al., Cancer Res. 56, 3055–3061 (1994); Hayden et al., Ther. Immunol. 1, 3–15 (1994)). In this case, however, there is no selection for the desired heterodimeric molecules, so that mainly bivalent homodimers are produced in this way. Expression of these molecules in functional form is, moreover, confined to eukaryotic cells.

In another group of molecules, the variable parts of the antibodies are fused to peptides or protein domains from other proteins to prepare bivalent or bispecific molecules (Plückthun and Pack, Immunotechnol. 3, 83–105 (1997)). In this case too there is usually formation of homo- and heterodimers because of the random association. In addition, these molecules contain a proportion, which is considerable in some cases, of foreign sequences, so that a marked immunogenicity is to be expected.

In a third group of molecules, slight modifications of recombinant Fv fragments, usually single-chain Fv fragments (scFv), are used to prepare bivalent or bispecific molecules (Holliger and Winter, Curr. Opin. Biotechnol. 4, 446–449 (1993)). These include dimerization through additional cysteines at the terminus of the scFv chains (MacCartney et al., Protein Engin. 8, 301–314 (1994)). However, this results in both homo- and heterodimers and, when expressed in bacterial cells, non-functional aggregates are produced. Tandem-scFv molecules of the structure scFv(A)-linker-scFv(B) (Mallender and Voss, J. Biol. Chem. 269, 199–206, 1994) can be expressed both in bacteria and in eukaryotic cells. However, in some of these cases non-functional associations of the four variable domains may also occur.

Recombinant antibody technology has led in recent years to the development of novel small, bivalent or bispecific antibody fragments. Examples of molecules of this type are the "diabodies" (Holliger et al., Proc. Natl. Acad. Sci. USA 90, 6444–6448, 1993). These comprise variable VH and VL domains of immunoglobulins which are connected together by a very short linker. This linker is too short to bring about association of the VH and VL domains of the same chain, as occurs with single-chain Fv fragments. This means that the VH and VL domains of two chains associate to form a dimer, so that molecules with two binding sites are produced (Perisic et al., Structure 2, 1217–1226, 1994). Bispecific "diabodies" are produced by the expression of two chains of the structure VH(A)-VL(B) and VH(B)-VL(A) in one cell. In this case, VL means the variable (V) domain of the light (L) chain and VH means the variable domain (V) of the heavy (H) chain of an immunoglobulin, these variable domains binding the antigen (A) or (B). The association of the VH parts with the VL parts produces heterodimeric fragments with functionally active binding sites. Bacterially expressed bispecific "diabodies" have already been employed successfully for recruiting various effector molecules, immunoglobulins, C1q or enzymes or effector cells such as, for example, cytotoxic T lymphocytes (Kontermann et al., Nature Biotechnol. 15, 629 (1997);

Holliger et al., Protein Engin. 9, 299 (1996); Nature Biotechnol. 15, 632 (1997), Zhu et al., BioTechnol. 14, 192 (1996); FitzGerald et al., Protein Engin. 10, 1221 (1997); Krebs et al., J. Biol. Chem. 273, 2858 (1998)).

"Diabodies", however, also have serveral disadvantages. For example since the two VH(A)-VL(B) and VH(B)-VL (A) chains are no longer physically connected, homo- and heterodimers can be produced in equal amounts. This makes very elaborate purification processes necessary for the heterodimers. In addition, dissociation of the dimers occurs, as has already been shown for scFv fragments (Glockshuber et al., Biochem. 29, 1362–1367 (1990)). To solve this problem, disulfide-stabilized "diabodies"(FitzGerald et al.,.Protein Engin. 10, 1221–1225, 1997) or "knob into hole diabodies" (Zhu et al., Protein Sci. 6, 781–788, 1997) have been developed. However, preparation thereof is associated with considerable complexity. In addition, genetic engineering expression of a bispecific "diabody" requires a signal sequence and a ribosome binding site for each chain, which is very complicated. Although non-equimolar amounts of the variable domains may be expressed, this increases the proportion of non-functional homodimers.

SUMMARY OF THE INVENTION

It is therefore an object of the present invention to find multiple antigen-binding molecules which do not have the described disadvantages of the so-called "diabodies" and which can be prepared in a simple manner in mainly homogeneous form.

One aspect of the present invention is therefore a single-chain multiple antigen-binding molecule comprising the following components:

a) a variable domain of a heavy chain of an immunoglobulin (VH) with a first specificity (A) or functional parts thereof, b) a variable domain of a light chain of an immunoglobulin (VL) with a second specificity (B) or functional parts thereof, c) a variable domain of a heavy chain of an immunoglobulin (VH) with the specificity (B) or functional parts thereof, and d) a variable domain of a light chain of an immunoglobulin (VL) with the specificity (A) or functional parts thereof, where the VH and VL domains are connected in the form of a VH-VL construct or VL-VH construct and the two VH-VL constructs are connected via a peptide (P).

Another aspect of the present invention is a recombinant nucleic acid molecule coding for a single-chain multiple antigen-binding molecule, a vector comprising the nucleic acid and a cell comprising the nucleic acid.

A further aspect of the present invention is a process for preparing a single-chain multiple antigen-binding molecule, which comprises cultivating a cell comprising an expression vector which comprises a nucleic acid encoding such a single chain multiple antigen binding molecule, and isolating the expression product where appropriate.

Other aspects of the present invention further include a pharmaceutical composition comprising a single-chain multiple antigen-binding molecule; a method for the diagnosis, prophylaxis or treatment of cancer, autoimmune diseases, inflammatory diseases, disorders of the blood, disorders of the nervous system or infectious diseases using the single chain multiple binding molecule.

BRIEF DESCRIPTION OF THE DRAWINGS

FIG. 8 B shows control experiments with a CEA-negative cell line (A549).

DETAILED DESCRIPTION OF THE INVENTION

Single-chain Multiple Antigen Binding Molecule in General

The present invention relates to a single-chain multiple antigen-binding molecule with diverse variable domains of a heavy and of a light chain of an immunoglobulin, which are connected in the form of a VH-VL construct, which are in turn connected together via a peptide. The present invention also relates to nucleic acid molecules encoding the single-chain multiple antigen-binding molecule, to a vector comprising the nucleic acid, to a cell that comprises the vector, and to the preparation and use thereof as pharmaceutical or diagnostic aid.

It is an object of the present invention to find multiple antigen-binding molecules which do not have the described disadvantages of the so-called "diabodies" and which can be prepared in a simple manner in mainly homogeneous form.

According to one aspect of the present invention, there is provided a single-chain multiple antigen-binding molecule comprising:

a) a variable domain of a heavy chain of an immunoglobulin (VH) with a first specificity (A) or functional parts thereof, b) a variable domain of a light chain of an immunoglobulin (VL) with a second specificity (B) or functional parts thereof, c) a variable domain of a heavy chain of an immunoglobulin (VH) with the specificity (B) or functional parts thereof, and d) a variable domain of a light chain of an immunoglobulin (VL) with the specificity (A) or functional parts thereof, where the VH and VL domains are connected in the form of a VH-VL construct or VL-VH construct and the two VH-VL constructs are connected via a peptide (P).

In an embodiment, the molecule according to the invention comprises more than two of said VH-VL constructs. This makes it possible to obtain molecules which comprise several specificities (A), (B), (C) etc.

Figure 1:
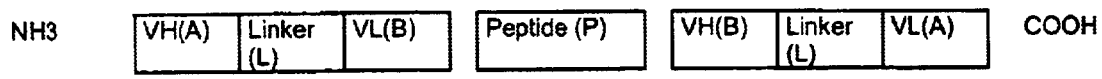
FIG. 1 describes diagrammatically the structure of a single-chain double antigen-binding molecule.

In a preferred embodiment, the individual VH-VL constructs are bound via their variable domains with the same specificity (i.e. VH(B)-peptide-VL(B)). A particularly preferred structure of a molecule according to the invention is depicted in FIG. 1.

In another preferred embodiment, the individual specificities are essentially identical. The term "essentially identical" means according to the present invention that it is perfectly possible for the domains to differ in molecular structure, but their specificity, i.e. the specific antigen-binding function, is retained. The result of this is that the molecule according to the invention may comprise not just a complete variable domain of a heavy or light chain of an immunoglobulin, but may also comprise functional parts thereof, i.e. the parts which have retained their specific antigen-binding property as determined through ELISA-assays or FACS sorting. For example, also included for the purpose of the present invention are artificial constructs composed of the individual complementary determining regions parts ("CDR") of variable domains of an immunoglobulin (Jones, P. T. et al. Nature, 321, 522, 1986; Riechmann, L. et al. Nature 332, 323, 1988; Verhoeyen, M. et al. Science, 239, 1534, 1988).

In a preferred embodiment, the VH and VL domains are connected via a peptide linker (L) in the form of a VH-L-VL construct or VL-L-VH construct. The linker should in this case generally be as short as possible, preferably about 1–20 amino acids in particular about 1–5 amino acids, long. A linker with the sequence GGGGS (SEQ ID NO: 1) is particularly preferred.

In contrast to the linker (L), the connecting peptide (P) can have any suitable length. However, a peptide (P) preferably has about 12–40 amino acids, in particular about 12–20 amino acids, especially about 14 amino acids. A particularly preferred peptide (P) comprises the amino acid sequence GGGGSGGRASGGGS (SEQ ID NO: 2) or GGGGSGGRASGGGGS (SEQ ID NO:3), and is especially a peptide (P) consisting of said amino acid sequence.

Effector Molecules

In another preferred embodiment, the molecule according to the invention comprises an effector (E) as a further component. This effector can be linked to the molecule according to the invention directly or, where appropriate, via a connector (B). It is particularly preferred for the connector (B) to comprise a protease cleavage sequence, preferably a PSA (prostate-specific antigen), cathepsin, plasminogen and/or plasminogen activator cleavage sequence.

The protease cleavage sequence is particularly preferred because this makes it possible to detach the effector from the molecule according to the invention by use of a protease. The separation is particularly advantageous when the activity of the effector is inhibited due to the effector being bound directly or indirectly by means of the connector to the molecule according to the invention.

Since proteases are present in particular in regions of inflammation or in tumors, the effectors, which are preferably inactivated because of their binding to the molecule according to the invention via a protease cleavage sequence, undergo extensive local release there. It is additionally possible by choosing suitable target structures for the molecule according to the invention, for example having a specificity for antigens on tumor cells, for antigens on tumor-associated endothelial cells or for antigens on inflammatory cells such as, for example, lymphocytes or macrophages, to achieve accumulation of the molecule according to the invention with the effector in the region of, for example, an inflammation or a tumor.

It is also possible according to the present invention for several effectors to be bound directly or indirectly to the molecule according to the invention.

Proteases or the relevant cleavage sequences are described in detail, for example in German patent application #DE1970430.1.

Figure 2:
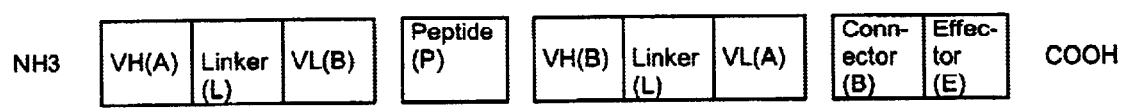
FIG. 2 describes diagrammatically a single-chain double antigen-binding molecule with an effector.

One example of a preferred molecule according to the invention having an effector which is bound via a connector to the molecule is depicted diagrammatically in FIG. 2.

Selection of Antigen Specificity

The selection of the individual components in the molecule according to the invention generally depends on the area of application.

If the molecule according to the invention is to be used as a diagnostic aid then, in a further embodiment, the first specificity (A) is directed against a molecule to be analyzed, and the second specificity (B) directly or indirectly against an analyte. The analyte can be, for example, a radioactive molecule, a fluorescent molecule or an enzyme which converts, through its enzymatic activity, a precursor of an analyte into an active analyte.

In another preferred embodiment, the first specificity (A), is directed against a molecule to be analyzed, the second specificity (B) against another molecule to be analyzed and the effector (E) is an analyte, for example a radioactive molecule, a fluorescent molecule and/or an enzyme, as already explained in detail above.

The molecule according to the invention can, however, also be used as ligand for target cell-specific binding of a viral or nonviral vector. In a preferred embodiment, the molecule according to the invention can be used as so-called multifunctional ligand. It is advantageous for this purpose if the peptide (P) and/or the effector (E) comprises a fusogenic peptide. The multifunctional ligand serves for target cell-specific transfer of nucleotide sequences and is generally a protein which comprises a target cell-specific ligand, a gene construct-specific ligand and a fusogenic peptide. Multifunctional ligands of this type can be used for specifically binding gene constructs, i.e. nucleic acid constructs, to a target cell, and the fusogenic peptide makes it possible for the nucleic acid construct to penetrate through the cell membrane into the cell nucleus and thus also be released from the endosome.

On use of the molecule according to the invention as ligands for a vector or as multifunctional ligands, it is advantageous for the first specificity (A) to be directed against a target cell and the second specificity (B) against a vector. The vector is generally a nucleic acid, a cationic peptide or protein, a cationic lipid, a cationic peptide or a cationic porphyrin. In a particular embodiment of this invention, the vector is a viral vector derived from, for example, adenoviruses (AdV), adeno-associated viruses (AAV), vaccinia virus, RSV, HSV, influenza virus or lentivirus.

Examples of target cell-specific ligands, of membrane structures on the target cell, of target-cell-specific ligands and of gene construct-specific ligands which are derived from immunoglobulins, i.e. comprise VH and VL domains, as well as of peptides with a fusogenic property are described in detail in DE19649645.4.

The molecule according to the invention is also suitable for prophylaxis and/or as therapeutic agent.

For these purposes, for example, the first specificity (A) is directed against a cell membrane such as, for example, against lymphocytes, macrophages, monocytes, granulocytes, hematopoietic cells, endothelial cells, smooth muscle cells, striped muscle cells, epithelial cells, liver cells, kidney cells, glia cells, cells of the supporting tissue, tumor cells or leukemia cells, or against proteins of the extracellular matrix, of the complement system, of the coagulation system, of the kinin system, of the blood plasma, of the supporting tissue, or against cytokines or chemokines, or against endogenous or exogenous toxins, or against pharmaceuticals, for example digitalis and/or against pathogens, such as, for example, bacterial, viral and/or parasitic pathogens.

The second specificity (B) can, for example, be directed against a cell membrane of, for example, lymphocytes, macrophages, monocytes or granulocytes, with the result that crosslinking thereof with a target structure can lead to cytotoxic, immunomodulating or inflammatory processes.

It can also be directed against cytokines, chemokines or growth factors, with the result that crosslinking thereof with a target structure may induce immunomodulating or proliferative processes. It may also be directed against proteins of the complement system which initiate, enhance or inhibit activation thereof. Crosslinking of a protein of this type with a target structure may, depending on the choice of the protein, induce inflammatory and cytolytic or antiinflammatory and cytoprotective reactions. It may also be directed against proteins of the coagulation system which initiate, enhance or inhibit activation thereof. Crosslinking of a protein of this type with the target structure may, depending on the choice of the protein, induce or prevent thromboses. It may furthermore be directed against fibrinolytic proteins which lead to dissolution of fibrin clot on the target structure, against enzymes which are able to convert the inactive precursor of a drug into an active, for example cytotoxic, drug on the target structure, against peptide hormones or steroid hormones, against the constant part of an immunoglobulin, against a mediator such as, for example, histamine, serotonin, leukotriene, prostacyclin or kinin, against pathogens, such as, for example, bacterial, viral and/or parasitic pathogens, or against tumor cells.

Cytokines as target structures, or monocytes, macrophages and/or lymphocytes as target structures can be crosslinked by the molecule according to the invention with infection or tumor antigens and thereby induce in vivo an enhanced immune response against the antigen. It is advantageous in this connection to add the particular antigen of the pathogen or of the tumor and, where appropriate, also the cytokine to the molecule according to the invention, and to administer or to inject locally the crosslinked complex.

The second specificity (B) can also be directed against endogenous or exogenous toxins so that either neutralization of the toxin and phagocytosis or else a toxic reaction on the target structure can be brought about. It may furthermore be directed against pharmaceuticals such as, for example, digitalis, so that complexation and elimination of the pharmaceutical can be brought about.

In another preferred embodiment, the molecule according to the invention with effector permits the crosslinking of two identical or different target structures with one or more effector(s).

Examples of suitable effectors are a transmembrane domain, a glycophospholipid anchor, the ligand-binding part of a receptor; the ligand for a receptor or the receptor-binding part-sequence of the ligand; a peptide hormone; a cytokine; a growth factor; a growth factor inhibitor; a chemokine; an interferon; a mediator; a peptide acting on the circulation; an enzyme which converts an inactive precursor of a drug into an active drug; a protein which activates or inhibits coagulation; a protein which activates or inhibits fibrinolysis; a protein which activates or inhibits the complement system; one or more constant domains of an immunoglobulin; a cytotoxic peptide, another single-chain, single or multiple, in particular double antigen-binding molecule; a tumor antigen or the antigen of a pathogen, such as, for example, a bacterial antigen or a viral antigen; a peptide comprising cysteine to produce dimers of the molecule according to the invention; and/or a di- or multimerizing peptide (Plückthun and Pack, Immunotechnol. 3, 83–105 (1997)).

Nucleic Acid Molecules and Vectors Encoding ScMAB

Another aspect of the present invention is a nucleic acid coding for a molecule according to the invention. The nucleic acid is generally a DNA or RNA, preferably a double-stranded DNA.

For the secretion, which is required where appropriate, of the expression product according to the invention, the nucleic acid according to the invention comprises at the 5' end a nucleotide sequence coding for a signal or transmembrane sequence (see, for example, DE19639103.2 or DE19651443.6). One example of suitable signal or transmembrane sequences is the signal sequence for immunoglobulin (DNA position$\leq$63 to $\geq$107), the signal sequence for CEA (DNA position$\leq$33 to $\geq$134) or the signal sequence of human respiratory syncytial virus glycoprotein (cDNA of the amino acid sequences$\leq$38 to $\geq$50 or 48 to 65).

Figure 3:
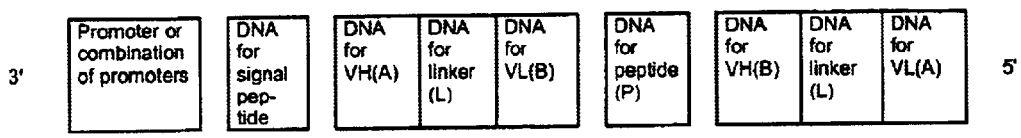
FIG. 3 describes diagrammatically nucleic acid constructs coding for a single-chain double antigen-binding molecule.
Figure 4:
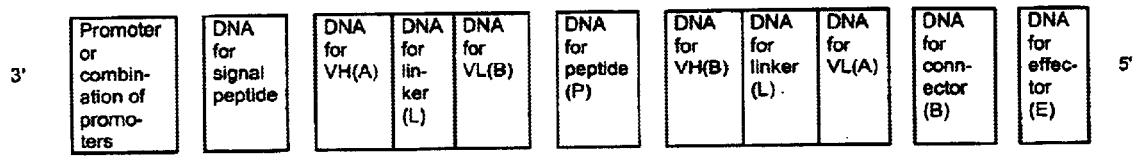
FIG. 4 describes diagrammatically a nucleic acid construct coding for a single-chain double antigen-binding molecule with effector.
Figure 5:
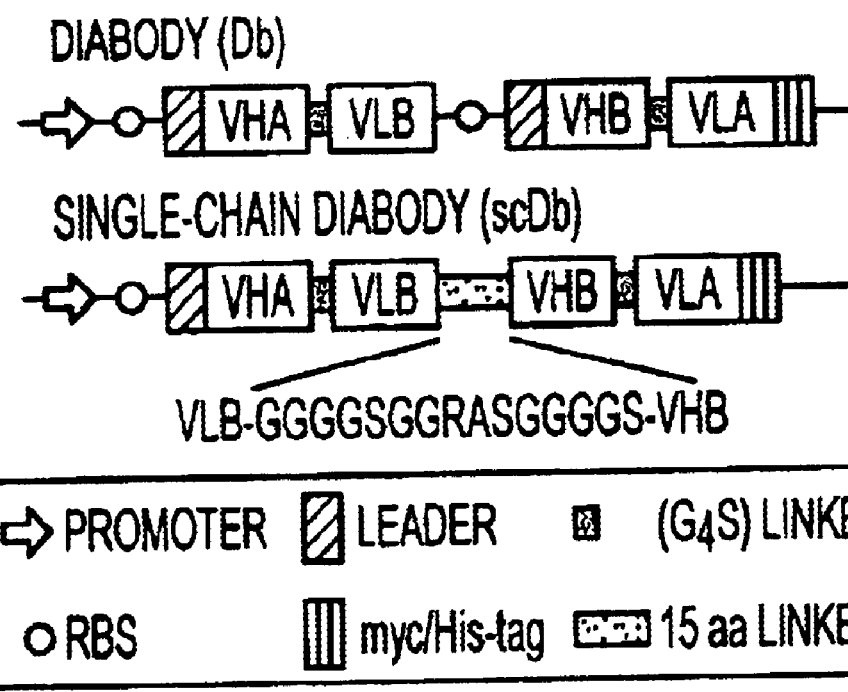
FIG. 5 compares diagrammatically the structures of a diabody and a single-chain double antigen-binding molecule.

In another embodiment, the nucleic acid according to the invention comprises at the 5' end a promoter and/or transcription activator binding sequence. The activator binding sequence can preferably be activated or suppressed cell-specifically, cell cycle-specifically, metabolism-specifically and/or by a drug. Activator sequences of this type, including combinations thereof, are described in EP97101507.8, DE19617851.7, DE19639103.2, DE19651443.6, DE19704301.1, EP97102547.3 and DE19710643.9. Particularly preferred nucleic acid constructs according to the invention are depicted diagrammatically in FIGS. 3 and 4.

In a preferred embodiment, the nucleic acid according to the invention comprises at the 5' end of the start codon the sequence GCCACC (SEQ ID NO: 17) or GCCGCC (SEQ ID NO: 18) which may bring about enhancement of translation.

Another embodiment of the present invention relates to a vector comprising the nucleic acid according to the invention. The vector can in this case be a viral or nonviral vector, preferably a nonviral vector, which is selected in particular from a cationic lipid, a cationic polymer, a cationic peptide or a cationic porphyrin.

To prepare the molecules according to the invention, the described nucleic acid is cloned into an expression vector, for example a suitable plasmid, and introduced into a suitable cell, for example into a bacterial, yeast, insect or mammalian cell, the cell transformed or transfected in this way is cultivated, and the expression product is isolated where appropriate. The methods are generally known to the skilled worker and are described in detail, for example, in Sambrook J. et al. Molecular Cloning, A Laboratory Handbook 2nd ed., Cold Spring Harbor Laboratory Press, 1989.

In a particular embodiment of the present invention, these cells express a molecule according to the invention having an effector, this effector preferably being a transmembrane domain.

Thus, for example, the DNA sequence coding for the transmembrane sequence of human macrophage colony-stimulating factor (DNA position$\leq$1485 to $\geq$1554) or the DNA sequence coding for the signal and transmembrane region of human respiratory syncytial virus (RSV) glycoprotein G (amino acids 1 to 63 or the part-sequence thereof amino acids 38 to 63) or the DNA sequence coding for the signal and transmembrane region of influenzavirus neuraminidase (amino acids 7 to 35 or the part-sequence amino acids 7 to 27) can be inserted between the promoter sequence and the DNA sequence of the molecule according to the invention or else at the 3' end of the gene.

However, in order to anchor the drug in the cell membrane of the cells expressing the molecule according to the invention, it is also possible to insert a nucleotide sequence coding for a glycophospholipid anchor into the nucleic acid construct.

Insertion of a glycophospholipid anchor generally takes place at the 3' end of the nucleotide sequence coding for the molecule according to the invention and can take place in addition to the insertion of a signal sequence.

Glycophospholipid anchors have been described, for example, for CEA, for N-CAM and for other membrane proteins such as, for example, Thy-1.

Owing to this transmembrane region, the particular cell expresses the molecule according to the invention on the cell membrane and thus acquires a "receptor" which is specific for the target or effector structures which are recognized by the antigen-binding parts of the molecule according to the invention.

Another preferred receptor is the transmembrane- or signal-transducing domain of a receptor, for example the T-cell receptor or the M-CSF receptor. This makes it possible for the cell expressing the molecule according to the invention on the cell membrane to be activated by binding of the target structures to specific functions. Specific functions of this type can be, for example, cytotoxic reactions of T lymphocytes, phagocytosis reactions of macrophages and granulocytes or exocytosis reactions of granulocytes, monocytes and macrophages.

Another aspect of the present invention is therefore a cell comprising a nucleic acid according to the invention or a vector according to the invention, in particular a bacterial, insect, yeast or mammalian cell. Suitable mammalian cells are, besides the generally known cells for expressing nucleic acids, such as, for example, CHO or BHK cells, also a lymphocyte, a macrophage, a glia cell, an epithelial cell, a liver cell, a kidney cell, a bone marrow cell, an endothelial cell, a smooth or striped muscle cell or a fibroblast.

The last-mentioned cells are suitable in particular for a gene therapy application because these cells which comprise the nucleic acid construct according to the invention can be injected into a patient locally or parenterally, for example intravenously, intraarterially, into a body cavity, into an organ or subcutaneously for prophylaxis or therapy of a disorder.

However, for treatment of disorders by gene therapy it is also possible to administer the nucleic acid constructs according to the invention directly to the patient locally, into a body cavity, into an organ, into the circulatory system, subcutaneously or intramuscularly.

Another aspect of the present invention is therefore also a pharmaceutical comprising a molecule according to the invention, a nucleic acid according to the invention, a vector according to the invention or a cell according to the invention, and a diagnostic aid comprising a molecule according to the invention, which is also directed against an analyte, as already described above in detail.

The molecule according to the invention, the nucleic acid according to the invention, the vector according to the invention or the cell according to the invention are thus suitable for the therapy, prophylaxis or diagnosis of, for example, oncoses, autoimmune diseases, inflammatory diseases, disorders of the blood, in particular of the blood coagulation and/or circulatory system, disorders of the nervous system and/or infectious diseases.

The choice of the individual components in this connection generally depends on the use of the items according to the invention. The individual components and the uses thereof are described in detail below, generally and by way of example:

To prepare an item according to the invention, it is possible, as already depicted by way of example in FIGS. 3 and 4, to link the nucleic acid construct according to the invention at its 5' end to the 3' end of a nucleic acid coding for a signal sequence, and to link the latter in turn at its 5' end to the 3' end of a promoter sequence.

The promoter sequences to be selected include, for example, promoters and activator sequences capable of unrestricted activation, such as, for example, the promoter of RNA polymerase III, the promoter of RNA polymerase II, the CMV promoter and/or enhancer, the SV40 promoter; or viral promoter and activator sequences such as, for example, HBV, HCV, HSV, HPV, EBV, HTLV, HIV.

On use of the HIV promoter, preferably the entire LTR sequence including the TAR sequence [Position$\leqq -453$ bis$\geqq -80$, Rosen et al., Cell 41, 813 (1985)] is employed as virus-specific promoter.

Other promoter sequences to be selected are, for example, promoter and enhancer sequences which can be activated metabolically, such as, for example, the enhancer inducible by hypoxia, promoters which can be activated cell cycle-specifically, such as, for example, the promoter of the cdc25C gene, of the cdc25B gene, of the cyclin A gene, of the cdc2 gene, of the B-myb gene, of the DHFR gene or of the E2F-1 gene, or else binding sequences for transcription factors which occur or are activated cell cycle-specifically. These binding sequences include, for example, binding sequences for c-myc proteins. Monomers or multimers of the nucleotide sequence referred to as the Myc E-Box [5'-GGAAGCAGACCACGTGGTCTGCTTCC-3'] (SEQ ID NO: 19) are included in these binding sequences.

Further promoter sequences to be selected are, for example, promoters which can be activated by tetracycline, such as, for example, the tetracycline operator in combination with a corresponding repressor, or chimeric promoters. A chimeric promoter is the combination of an activator sequence which can be activated cell-specifically, metabolically or virus-specifically and is located upstream, with a promoter module which is located downstream and which comprises the CDE-CHR or E2FBS-CHR nucleotide sequence, to which suppressor proteins bind and are thereby able to inhibit activation of the activator sequence located upstream in the $G_0$ and $G_1$ phases of the cell cycle (WO96/06943; Lucibello et al., EMBO J. 14, 132 (1995)).

Other promoter sequences to be selected are, for example, promoters which can be activated cell-specifically, such as, preferably, promoters or activator sequences from promoters or enhancers of genes which code for proteins which are preferably produced in selected cells.

For example, promoters for the following proteins are preferably to be used for the purpose of the invention in the following cells:

Promoter and activator sequences which are activated in endothelial cells are gene-regulatory sequences from genes which code, for example, for the following proteins: brain-specific endothelial glucose 1 transporter, endoglin, VEFG receptor 1 (flt-1), VEGF receptor 2 (flk-1, KDR), til-1 or til-2, B61 receptor (Eck receptor), B61, endothelin, specifically endothelin B or endothelin 1, endothelin receptors, especially the endothelin B receptor, mannose 6-phosphate receptors, von Willebrand factor, IL-1α, IL-1β, IL-1 receptor, vascular cell adhesion molecule (VCAM-1) or synthetic activator sequences which consist of oligomerized binding sites for transcription factors which are preferentially or selectively active in endothelial cells. One example thereof is the transcription factor GATA-2 whose binding site is 5'-TTATCT-3' in the endothelin 1 gene.

Promoters or activator sequences activated in cells in the neighborhood of activated endothelial cells are gene-regulatory sequences from genes which code, for example, for the following proteins: VEGF, in which case the gene-regulatory sequences for the VEGF gene are the 5'-flanking region, the 3'-flanking region, the c-Src gene or the v-Src gene, or steroid hormone receptors and their promoter elements, especially the mouse mammary tumor virus promoter.

Promoters or activator sequences which are activated in muscle cells, especially smooth muscle cells, are gene-regulatory sequences from genes which code, for example, for the following proteins: tropomyosin, α-actin, α-myosin, receptor for PDGF, receptor for FGF, MRF4, phosphofructokinase A, phosphoglycerate mutase, troponin C, myogens, receptors for endothelin A, desmin, VEGF (see above), "artificial" promoters, or promoters of muscle-specific transcription factors such as factors of the helix-loop-helix (HLH) family (MyoD, Myf-5, myogens, MRF4) or the zinc finger protein GATA4.

The HLH proteins, and GATA-4, show muscle-specific transcription not only with promoters of muscle-specific genes but also in the heterologous context, and thus also with artificial promoters. Examples of artificial promoters of this type are multiple copies of the (DNA) binding site for muscle-specific HLH proteins such as the E box (Myo D) (for example 4x AGCAGGTGTTGGGAGGC) (SEQ ID NO: 5) or multiple copies of the DNA binding site for GATA-4 of the α-myosin heavy chain gene (for example 5'-GGCCGATGGGCAGATAGAGGGGGCCGATGGGCA GATAGAGG3') (SEQ ID NO: 6).

Promoters and activator sequences which are activated in glia cells are, for example, gene-regulatory sequences from genes which, for example, code for the following proteins: the Schwann cell-specific protein periaxin, glutamine synthetase, the glia cell-specific protein (glial fibrillary acid protein=GFAP), the glia cell protein S100b, IL-6, CNTF, 5-HT receptors, TNFα, IL-10, insulin-like growth factor receptor I and II or VEGF (see above).

Promoters and activator sequences which are activated in blood-forming cells are, for example, promoter sequences for genes of a cytokine or its receptor which are expressed in blood-forming cells or in adjacent cells such as, for example, the stroma.

These include promoter sequences from genes which, for example, code for the following cytokines and their receptors: stem cell factor receptor, stem cell factor, IL-1α, IL-1 receptor, IL-3, IL-3 receptor (α subunit), IL-3 receptor (β subunit), IL-6, IL-6 receptor, GM-CSF, GM-CSF receptor (α chain), interferon regulatory factor 1 (IRF-1), with the promoter of IRF-1 being activated to the same extent by IL-6 as by IFNγ or IFNβ, erythropoietin or erythropoietin receptor.

Promoters and activator sequences which are activated in lymphocytes and/or macrophages are, for example, the promoter and activator sequences of the genes coding for cytokines, cytokine receptors and adhesion molecules and receptors for the Fc fragment of antibodies, such as, for example, IL-1 receptor, IL-1α, IL-1β, IL-2, IL-2 receptor, IL-3, IL-3 receptor (α subunit), IL-3 receptor (β subunit), IL-4, IL-4 receptor, IL-5, IL-6, IL-6 receptor, interferon regulatory factor 1 (IRF-1), the promoter of IRF-1 being activated to the same extent by IL-6 as by IFNγ or IFNβ, IFNγ responsive promoter, IL-7, IL-8, IL-10, IL-11, IFNγ, GM-CSF, GM-CSF receptor (α chain), IL-13, LIF, macrophage colony stimulating factor (M-CSF) receptor, type I and II macrophage scavenger receptors, MAC-1 (leukocyte function-associated antigen), LFA-1α (leukocyte function-associated antigen) or p150,95 (leukocyte function-associated antigen).

Promoter and activator sequences which are activated in synovial cells are, for example, the promoter sequences of genes coding for matrix metalloproteinases (MMP), such as, for example, MMP-1 (interstitial collagenase), MMP-3 (stromelysin/transin) or tissue inhibitors of metalloproteinases (TIMP) such as TIMP-1, TIMP-2, TIMP-3.

Promoters and activator sequences which are activated in leukemia cells are, for example, promoters of genes which code for the following proteins: HSP-70, bcl-1/cyclin D-1, bcl-2, IL-6, IL-10, TNFα, TNFβ, HOX-11, BCR-Abl, E2A-PBX-1, PML-RAR (promyelocytic leukemia retinoic acid receptor) or c-myc, where c-myc proteins bind to and activate multimers of the nucleotide sequence referred to as the Myc E box (5'-GGAAGCAGACCAGCTGGTCTGCTTCC-3') (SEQ ID NO: 7).

Promoters or activator sequences which are activated in tumor cells are, for example, gene-regulatory nucleotide sequences with which transcription factors formed or active in tumor cells interact.

For the purpose of this invention, the preferred promoters or activator sequences include gene-regulatory sequences or elements of genes which encode proteins particularly produced in cancer cells or sarcoma cells. Thus, preferably used for small-cell bronchial carcinomas is the promoter of the N-CAM protein, for ovarian carcinomas is the promoter of the hepatitis growth factor receptor or of L-plastin, and for pancreatic carcinomas is the promoter of L-plastin or of polymorphic epithelial mucin (PEM).

A considerable advantage of the present invention is that the linkage of the individual components favours heterodimeric association so that there is predominantly formation of single-chain multiple antigen-binding molecules. There is also a reduction in the dissociation of the dimers, as has been shown for scFv fragments (see, for example, Glockshuber et al., Biochem. 29, 1362–1367, 1990). It is thus possible to prepare the molecules according to the invention with less complexity and in a more homogeneous form than the so-called "diabodies", even if the latter are disulfide-stabilized or in the form of "knob into hole diabodies".

In addition, only one signal sequence and one ribosome binding site (RBS) are necessary for preparing the molecule according to the invention. In contrast to this, a signal sequence and an RBS are required for each chain in the "diabodies" according to the invention. Another advantage of the present invention is that with the molecules according to the invention there is expression of equimolar amounts of the variable domains, whereas on expression of the two chains of "diabodies" there may be production of non-equimolar amounts and thus the proportion of non-functional homodimers is increased.

Another advantage of the molecule according to the invention is that it can be expressed simply and in functional form both in bacteria and in yeasts, baculoviruses and other eukaryotic cells. Moreover, besides secretion of the molecules according to the invention, there is also the possibility of expressing them inside cells or in association with membranes (see, for example, Biocca & Cattaneo, Trends Cell Biol. 5, 248–252 (1995)).

Another advantage of the molecules according to the invention is that they can be employed widely both as diagnostic aid, and as drug for the prophylaxis and/or therapy of a disorder, like bispecific antibodies.

The genes of effectors and promoter sequences are to be selected with a view to the desired use and taking account of the target cell to be transduced. For example, the combinations of promoter sequences and genes for effectors to be chosen for the following disorders are the following:

Use of ScMAB in Tumor Therapy

The target cells for tumor therapy are, for example, proliferating endothelial cells, or the stroma cells and muscle cells adjacent to the endothelial cell, or tumor cells or leukemia cells, the promoters used are, for example, endothelial cell-specific and cell cycle-specific, or cell-nonspecific or muscle cell-specific and cell cycle-specific, or tumor cell-specific (solid tumors, leukemias) and cell cycle-specific promoters, and the effectors used are, for example, the following genes:

Genes of inhibitors of cellular proliferation are, for example, of retinoblastoma protein (pRb=p110) or the related p107 and p130 proteins. Retinoblastoma protein (pRb/p110) and the related p107 and p130 proteins are inactivated by phosphorylation. The genes of cell cycle inhibitors which should preferably be used are those having mutations for the inactivation sites of the expressed proteins, without the latter's function being impaired thereby. Examples of these mutations are described for p110. The DNA sequence for the p107 protein or the p130 protein is mutated in an analogous manner. The gene of the p53 protein is also suitable. The p53 protein is inactivated in the cell either by binding to specific proteins such as, for example, MDM2, or by oligomerization of the p53 via the dephosphorylated C-terminal serine. Thus preference is given to the use of a DNA sequence for a p53 protein which is truncated by serine 392 at the C terminus. Further suitable genes are the gene of p21 (WAF-1), of the p16 protein, of other cdk inhibitors, of the GADD45 protein or of the bak protein.

Genes of coagulation-inducing factors and angiogenesis inhibitors are, for example, of plasminogen activator inhibitor 1 (PAI-1), PAI-2, PAI-3, angiostatin, interferons (IFNα, IFNβ or IFNγ), platelet factor 4, IL-12, TIMP-1, TIMP-2, TIMP-3, leukemia inhibitory factor (LIF) or tissue factor (TF) and its coagulation-promoting fragments.

Genes of cytostatic and cytotoxic proteins, are, for example, of perforin, granzyme, IL-2, IL-4, IL-12, interferons such as, for example, IFN-α, IFNγ or IFNγ, TNF, such as TNFα or TNFβ, oncostatin M, sphingomyelinase or magainin and magainin derivatives.

Genes of inducers of inflammations are, for example, of IL-1, IL-2, RANTES (MCP-2) monocyte chemotactic and activating factor (MCAF), IL-8, macrophage inflammatory protein I (MIP-1α, -β), neutrophil activating protein-2 (NAP-2), IL-3, IL-5, human leukemia inhibitory factor (LIF), IL-7, IL-11, IL-13, GM-CSF, G-CSF, M-CSF, cobra venom factor (CVF) or part-sequences of CVF which functionally correspond to human complement factor C3b, i.e. which are able to bind to complement factor B and, after cleavage by factor D, represent a C3 convertase, human complement factor C3 or its part-sequence C3b, of cleavage products of human complement factor C3 which resembles CVF functionally and structurally, or of bacterial proteins which activate complement or induce inflammations, such as, for example, porins of Salmonella typhimurium, clumping factors of Staphylococcus aureus, modulins in particular of Gram-negative bacteria, major outer membrane protein of legionellae or of Haemophilus influenza type B or of klebsiellae or M molecules of group G streptococci.

Genes of enzymes for activating precursors of cytostatics are, for example, of enzymes which cleave inactive precursors (prodrugs) into active cytostatics (drugs). Substances of this type and the prodrugs and drugs relevant to each of them have already been reviewed by Deonarain et al. (Br. J. Cancer 70, 786 (1994)), Mullen (Pharmac. Ther. 63, 199 (1994)) and Harris et al. (Gene Ther. 1, 170 (1994)). For example, the DNA sequence of one of the following enzymes can be used: herpes simplex virus thymidine kinase, varicella zoster virus thymidine kinase, bacterial nitroreductase, bacterial β-glucuronidase, plant β-glucuronidase from Secale cereale, human β-glucuronidase, human carboxypeptidase (CB), for example mast cell CB-A, pancreatic CB-B or bacterial carboxypeptidase, bacterial β-lactamase, bacterial cytosine deaminase, human catalase or peroxidase, phosphatase, especially human alkaline phosphatase, human prostatic acid phosphatase or type 5 acid phosphatase, oxidase, in particular human lysyl oxidase or human D-amino acid oxidase, in particular human glutathione peroxidase, human eosinophilic peroxidase or human thyroid peroxidase, β-galactosidase or α-galactosidase. Particular preference is given to a β-galactosidase for converting the prodrug daunomycin β-D-galactopyranoside into the cytostatic daunomycin.

Use of ScMAB In Therapy of Autoimmune Diseases and Inflammations

The target cells for the therapy of autoimmune diseases and inflammations are, for example, proliferating endothelial cells or macrophages and/or lymphocytes or synovial sells, the promoters used are, for example, endothelial cell-specific and cell cycle-specific, or macrophage- and/or lymphocyte-specific and/or cell cycle-specific, or synovial cell-specific and/or cell cycle-specific promoters, and the effectors used are, for example, the following genes:

Genes for allergy therapy are, for example, of IFNβ, IFNγ, IL-10, antibodies or fragments of antibodies against IL-4, soluble IL-4 receptors, IL-12 or TGFβ.

Genes for preventing the rejection of transplanted organs are, for example, of IL-10, TGFβ, soluble IL-1 receptors, soluble IL-2 receptors, IL-1 receptor antagonists or soluble IL-6 receptors.

Genes for the therapy of antibody-mediated autoimmune diseases are, for example, of TGFβ, IFNα, IFNβ, IFNγ, IL-12, soluble IL-4 receptors, soluble IL-6 receptors, immunosuppressant antibodies or $V_H$ and $V_L$-containing fragments thereof.

Genes for the therapy of cell-mediated autoimmune diseases are, for example, of IL-6, IL-9, IL-10, IL-13, TNFα or TNFβ, IL-13, an immunosuppressant antibody or its $V_H$- and $V_L$-containing fragments.

Genes of inhibitors of cell proliferation, cytostatic or cytotoxic proteins and enzymes for activating precurcors of cytostatics have already been described in detail above.

Genes for arthritis therapy are, for example, structural genes whose expressed protein inhibits inflammation, for example in the joint, directly or indirectly and/or promotes reconstitution of extracellular matrix (cartilage, connective tissue) in the joint.

These include, for example, IL-1 receptor antagonist (IL-1-RA) because IL-1-RA inhibits the formation of IL-1α, β; soluble IL-1 receptor because soluble IL-1 receptor binds and inactivates IL-1; L-6 because IL-6 increases the secretion of TIMP and superoxides and reduces the secretion of IL-1 and TNFα by synovial cells and chondrocytes; soluble TNF receptor because soluble TNF receptor binds and inactivates TNF; IL-4 because IL-4 inhibits the formation and secretion of IL-1, TNFα and MMP; IL-10 because IL-10 inhibits the formation and secretion of IL-1, TNFα and MMP and increases the secretion of TIMP; insulin-like growth factor (IGF-1) because IGF-1 stimulates the synthesis of extracellular matrix; TGFβ, in particular TGFβ1 and TGFβ2, because TGFβ stimulates the synthesis of extracellular matrix; superoxide dismutase or TIMP, in particular TIMP-1, TIMP-2 or TIMP-3.

Use of ScMAB in Treatment in Blood-Forming System

The target cells for the therapy of deficient formation of blood cells are, for example, proliferating immature cells of the blood-forming system or stroma cells adjacent to the blood-forming cells; the promoters used are, for example, promoters which are specific for blood-forming cells and/or cell cycle-specific, or cell nonspecific and cell cycle-specific, and the effectors used are, for example, the following genes: genes for anemia therapy are, for example, of erythropoietin.

Genes for leukopenia therapy are, for example, of G-CSF, GM-CSF or M-CSF.

Genes for thrombocytopenia therapy are, for example, of IL-3, leukemia inhibitory factor (LIF), IL-11 or thrombopoietin.

Use of ScMAB in Therapy of the Nervous System Disorders

The target cells for therapy of damage to the nervous system are, for example, glia cells or proliferating endothelial cells, the promoters used are, for example, glia cell-specific and cell cycle-specific or endothelial cell-specific and cell cycle-specific, or nonspecific and cell cycle-specific promoters, and the effectors used are, for example, the following genes:

Genes for neuronal growth factors are, for example, of FGF, nerve growth factor (NGF), brain-derived neurotrophic factor (BDNF), neurotrophin-3 (NT-3), neurotrophin-4 (NT-4) or ciliary neurotrophic factor (CNTF).

Genes for enzymes are, for example, genes of tyrosine hydroxylase or dopa decarboxylase.

Genes for cytokines and their inhibitors which inhibit or neutralize the neurotoxic effect of TNFα are, for example, of TGFβ; of soluble TNF receptors because TNF receptors neutralize TNFα; of IL-10 because IL-10 inhibits the formation of IFNγ, TNFα, IL-2 and IL-4; of soluble IL-1 receptors such as IL-1 receptor I or IL-1 receptor II because soluble IL-1 receptors neutralize the activity of IL-1; of the IL-1 receptor antagonist or of soluble IL-6 receptors.

Use of ScMAB in Therapy of Blood Coagulation and Circulatory Disorders

The target cells for the therapy of disturbances of the blood coagulation and circulatory system are, for example, endothelial cells, proliferating endothelial cells, somatic cells in the neighborhood of endothelial cells and smooth muscle cells or macrophages, the promoters used are, for example, cell-nonspecific and cell cycle-specific promoters, or promoters specific for endothelial cells, smooth muscle cells or macrophages and cell cycle-specific, and the effectors used are, for example, the following genes:

Genes for inhibiting coagulation or for promoting fibrinolysis are, for example, of tissue plasminogen activator (tPA), urokinase-type plasminogen activator (uPA), of hybrids of tPA and uPA, of protein C, hirudin, of serine proteinase inhibitors (serpins), such as, for example, C-1S inhibitor, α1-antitrypsin or antithrombin III, or of tissue factor pathway inhibitor (TFPI).

Genes for promoting coagulation are, for example, of F VIII, F IX, von Willebrand factor, F XIII, PAI-1, PAI-2 or tissue factor and fragments thereof.

Genes for angiogenesis factors are, for example, of VEGF or FGF.

Genes for lowering blood pressure are, for example, of kallikrein or endothelial cell "nitric oxide synthase".

Genes for inhibiting the proliferation of smooth muscle cells after injuries to the endothelial layer are, for example, of an antiproliferative, cytostatic or cytotoxic protein or of an enzyme for splitting precursors of cytostatics into cytostatics as already stated above, or of a fusion protein of one of these drugs with a ligand, for example an antibody or antibody fragments, which is specific for muscle cells.

Genes for other blood plasma proteins are, for example, of albumin, C1 inactivator, serum cholinesterase, transferrin or 1-antitrypsin.

Use of ScMAB for Prophylaxis or Therapy of Infectious Diseases

Target cells for inoculations are, for example, muscle cells or macrophages and/or lymphocytes, the promoters used are, for example, nonspecific and cell cycle-specific or target cell-specific and cell cycle-specific promoters, and the effectors used are, for example, genes for the prophylaxis of infectious diseases.

The active substance selected is generally the DNA of a protein which is produced by the pathogen and which leads, by injecting an immune response, i.e. through antibody binding and/or through cytotoxic T-lymphocytes, to neutralization and/or killing of the pathogen. So-called neutralizing antigens of this type are already in use as vaccine antigens (see, for example, Ellis, Adv. Exp. Med. Biol. 327, 263 (1992)).

Preferred for the purpose of the invention is a nucleic acid coding for neutralizing antigens of the following pathogens: influenza A virus, HIV, rabies virus, HSV (herpes simplex virus), RSV (respiratory syncytial virus), parainfluenza virus, rotavirus, VZV (varicella zoster virus), CMV (cytomegalovirus), measles virus, HPV (human papilloma virus), HBV (hepatitis B virus), HCV (hepatitis C virus), HDV (hepatitis D virus), HEV (hepatitis E virus), HAV (hepatitis A virus), Vibrio cholerae antigen, Borrelia burgdorferi, Helicobacter pylori or malaria antigen.

Active substances of this type for the purpose of the present invention also include the DNA of an anti-idiotype antibody or of its antigen-binding fragments, of which antibody the antigen-binding structures (the complementarity determining regions) represent copies of the protein or carbohydrate structure of the neutralizing antigen of the pathogen (see above).

Anti-idiotype antibodies of this type and their cleavage products can replace in particular carbohydrate antigens for bacterial pathogens and are reviewed, for example, by Hawkins et al. (J. Immunother. 14, 273 (1993)) and Westerink and Apicella (Springer Seminars in Immunopathol. 15, 227 (1993)).

Examples of other effectors are genes of "tumor vaccines". These include antigens on tumor cells, as reviewed, for example, by Sedlacek et al., Contrib. to Oncol. 32, Karger Verlag, Munich (1988) and Contrib. to Oncol 43, Karger Verlag, Munich (1992).

Other examples are the genes of the following antigens or of the following anti-idiotype antibodies: sialyl-Lewis; peptides on tumors which are recognized by T cells; proteins expressed by oncogenes; blood group antigens and their precursors; antigens on polymorphic epithelial mucin; or antigens on heat shock proteins.

The target cells for the therapy of chronic infectious diseases are, for example, liver cells, lymphocytes and/or macrophages, epithelial cells or endothelial cells, the promoters used are, for example, virus-specific or cell-specific and cell cycle-specific promoters, and the effectors used are, for example, the following genes:

Genes coding for a protein which has cytostatic, apoptotic or cytotoxic effects, or coding for an enzyme which cleaves a precursor of an antiviral or cytotoxic substance into the active substance.

Genes coding for antiviral proteins such as antivirally active cytokines and growth factors such as, for example, IFNα, IFNβ, IFN-γ, TNFα, TNFα, IL-1 or TGFβ, or antibodies with a specificity which inactivates the particular virus or its $V_H$ and $V_L$ containing fragments or its $V_H$ and $V_L$ fragments connected via a linker, as already described. Examples of antibodies against viral antigens are: anti-HBV, anti-HCV, anti-HSV, anti-HPV, anti-HIV, anti-EBV, anti-HTLV, anti-coxsackievirus or anti-hantavirus.

Another antivirally active protein is a rev-binding protein. These proteins bind to the rev RNA and inhibit rev-dependent post-transcriptional stages of retrovirus gene expression. Examples of rev-binding proteins are RBP9-27, RBP1-8U, RBP1-8D or pseudogenes of RBP1-8.

Genes coding for antibacterial proteins such as, for example, antibodies which neutralize bacterial toxins or opsonize bacteria. Examples of these are antibodies against meningococci C or B, *E. coli,* Borrelia, Pseudomonas, *Helicobacter pylori* or *Staphylococcus aureus.*

The following figures and examples are intended to illustrate the invention in detail. It should be understood, however, that the invention is not to be limited to the specific conditions or details described in these examples. Throughout the specification, any and all references to publicly available documents are specifically incorporated by reference.

EXAMPLES

Example 1

Preparation and Bacterial Expression of a Single-chain Double Antigen-binding Protein The preparation of a single-chain double antigen-binding protein is described using the example of a protein which recognizes the antigens carcinoembryonic antigen (CEA) and *E. coli* β-galactosidase.

The following DNA sequences were connected together in the 5' to 3' direction as follows:

LacZ promoter bacterial ribosome binding structure (AAGGAG)

bacterial signal sequence peIB (Power et al., Gene 113, 95–99 (1992))

VH anti-CEA (Kontermann et al., Immunotechnol. 3, 137 (1997))

linker GGGS (SEQ ID NO: 19)(Kontermann et al., (1997))

VL anti-β-galactosidase (Kontermann et al., (1997))

connecting peptide GGGGSGGRASGGGGS (SEQ ID NO: 3)

VH anti-β-galactosidase (Kontermann et al., (1997))

linker GGGGS (SEQ ID NO: 1)

VL anti-CEA (Kontermann et al., (1997))

Myc epitope for antibody 9E10 EQKLISEEDLN (SEQ ID NO: 8) (Munro & Pelham, Cell 46, 291–300 (1986))

polyhistidine HHHHHH (SEQ ID NO: 9) purification by IMAC (Kontermann et al., (1997))

The linkage of the construct was made possible by suitable restriction sites which were included via PCR amplification at the termini of the various DNA sequences (Kontermann et al., Immunotechnol. 3, 137 (1997)).

The linkage took place using enzymes specific for the restriction sites, and DNA ligases, known to the skilled worker. The enzymes can be purchased commercially. The construct was cloned into the bacterial expression vector pAB1 (Kontermann et al., (1997)).

The cloning was done using the oligonucleotide primers LMB2 and LMB3 (Kontermann, R. E. (1997), supra) and VK-NotFor: 5'-TTG TTC TGC GGC CGC CCG TTT CAG CTC CAG CTT GGT GCC AGC ACC-3'  (SEQ ID NO: 10)

scDb-AscBack: 5'-TGC ATG CTA GGG CGC GCC TCG GGC GGA GGT GGC TCA CAG GTG CAG CTG GTG CAA TCT GG-3'  (SEQ ID NO: 11)

scDb-AscForK: GCT CGG TAA GGC GCG CCC ACC GCT GCC ACC GCC TCC ACC TAG GAC GGT CAG CTT GGT CCC-3'  (SEQ ID NO: 12)

and peIB-Metminus: 5'-TTA CTC GCG GCC CAG CCG GCC ACG GCC CAG GT-3'  (SEQ ID NO: 13)

For this purpose, the fragments VHB-VLA (fragment 1) and VHA-VLB (fragment 2) from the diabody CEAGal (Kontermann, R. E. (1997)) were amplified using the primers LMB2 and LMB3 and were gel-purified. Fragment 1 was then amplified using the primers VK-NotFor and scDb-AscBack in order to introduce an AscI site and 7 amino acids of the linker. Fragment 2 was amplified using the primers LMB3 and scDb-AscForλ in order to introduce an AscI site and 8 amino acids of the linker. The fragments were hydrolyzed with AscI and NotI (fragment 1) and SfiI and AscI (fragment 2) and cloned into the bacterial expression vector pAB1 (Kontermann, R. E. (1997)). The resulting insert encodes a single-chain polypeptide in which VHA-VLB is connected via a 15 amino acid-long linker with the sequence GGGGSGGRASGGGGS (SEQ ID NO: 3) to VHB-VLA.

The plasmid was then inserted into TG1 bacteria, and these were cultivated by methods familiar to the skilled worker (Kontermann et al., (1997)).

The bacteria were disrupted and the single-chain double antigen-binding protein was purified from the periplasmic preparation by immobilized metal affinity chromatography (IMAC) (Hochuli et al., Bio/Techn. 6, 1321–1325 (1988)). Details of this method are described by Kontermann et al., (1997).

Figure 6:
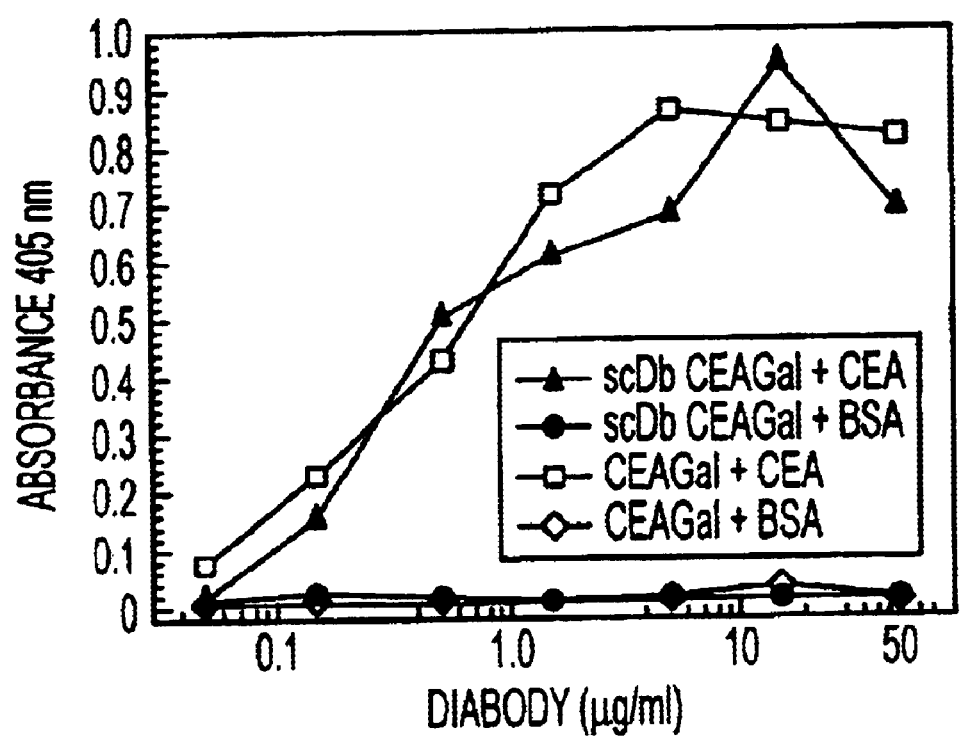
FIG. 6 shows the recruitment of β-galactosidase on plastic-bound CEA through the single-chain double antigen-binding protein according to the invention (scDb-CEAGal), compared with diabodies against CEA and E. coli β-galactosidase (CEAGal). A microtiter plate was coated with BSA as negative control.

The purified protein has a molecular weight of 60 kDa as has been shown by SDS polyacrylamide gel electrophoresis and gel filtration. It has been possible to purify about 200–300 μg of this molecule per liter of bacterial culture. The bacterially expressed single-chain double antigen-binding protein reacts in an ELISA with CEA and β-galactosidase and was able to recruit the enzyme to plastic-bound CEA, as has been shown by the conversion of o-nitrophenyl β-D-galactopyranoside (FIG. 6). In addition, this single-chain double antigen-binding protein was able to stain living and fixed CEA-expressing LoVo cells by recruitment of β-galactosidase and conversion of the substrate 5-bromo-4-chloro-3-indolyl β-D-galactopyranoside (X-Gal). For this, LoVo cells were incubated with 10 μg/ml of the appropriate antigen-binding protein with 10 μg/ml β-galactosidase and X-Gal (0.8 mg/ml in PBS, 3 mM potassium iron(III) cyanide, 3 mM potassium iron(II) cyanide). No staining was observed with various control cells (A549, HEK293) or with a diabody against hen's egg lysozyme and β-galactosidase (HELGal; Kontermann et al., (1997)).

Example 2
Eukaryotic Expression of a Single-chain Double Antigen-binding Protein For expression in eukaryotic cells, the coding region of the single-chain double antigen-binding protein was cloned into a eukaryotic expression vector (pSecTagA, Invitrogen), the bacterial signal sequence having been replaced by the Ig-κ signal sequence already present in the vector.

For this, the single-chain construct was amplified using the primers LMB2 and pelB-Metminus, whereby methionine in the pelB leader (position 21) was replaced by threonine. This was followed by hydrolysis with SfiI and EcoRI and cloning into the vector pSecTagA. The mature single-chain antigen-binding protein contains 7 additional amino acids (AAQPATA) (SEQ ID NO: 14) at the N terminus of the VHA domain.

Figure 7:
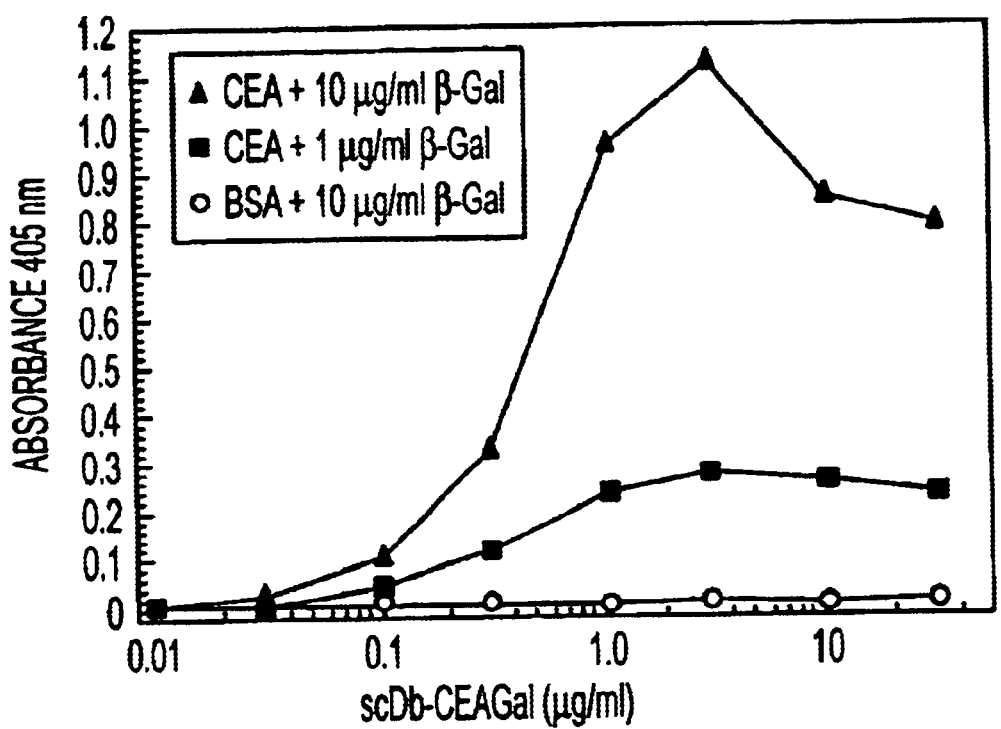
FIG. 7 shows the recruitmant of β-galactosidase through scDb-CEAGal, secreted by mammalian cells, with different amounts of scDb-CEAGal and β-galactosidase being employed in CEA-coated microtiter plates. The substrate employed was o-nitrophenyl β-D-galactopyranoside. A microtiter plate was coated with BSA as negative control.

The plasmid was transiently transfected with Lipofectamine (Gibco) into eukaryotic HEK 293 cells. Stable cells were selected in the presence of zeocin. It was possible in immunofluorescence experiments with these cells to detect staining of the endoplasmic reticulum ER and of the Golgi apparatus. It was further possible to detect secretion of the single-chain double antigen-binding protein by immunoprecipitation of a 60 kDa protein from the supernatant of $^{35}$S-Met-labeled cells and by purification by immobilized metal affinity chromatography (IMAC). The purified protein is functionally active in the binding of β-galactosidase and CEA-coated microtiter plates and in the recruitment of β-galactosidase to plastic-bound CEA (FIG. 7).

Example 3
In vitro enzyme recruitment by cocultivation with cells secreting single-chain double antigen-binding protein Recruitment was investigated in vitro by cocultivation of HEK 293 cells producing the single-chain double antigen-binding protein and CEA-positive LoVo cells. For this, firstly the cells producing the protein according to the invention were cultivated with the LoVo cells in Transwell cell culture dishes (Costar) in which the two cell lines are separated by a membrane. After two days, β-galactosidase (10 μg/ml) was added, and the recruitment was detected by adding the substrate X-Gal. A specific staining was found on cocultivation with the cells producing the single-chain double antigen-binding protein, whereas control experiments with untransfected HEK 293 cells showed no staining.

Experiments in which the LoVo cells were replaced by A549 cells (CEA-negative), and experiments in which the cells producing the single-chain double antigen-binding protein were incubated with enzyme and substrate, were likewise negative. The latter illustrates that the cells producing the single-chain double antigen-binding protein are not themselves able to bind the enzyme.

In another experiment, the HEK 293 cells secreting the single-chain double antigen-binding protein, and the LoVo cells were cocultivated directly with an inoculation ratio of from 1:4 to 1:24. In order to distinguish the HEK 293 cells from the LoVo cells, the former were stained with CM-DiI (Molecular Probes) (red fluorescence) before addition of the LoVo cells. After two days, β-galactosidase was added, and the binding to cells was detected by adding X-Gal (10 μg/ml) and by direct immunofluorescence with an anti-β-galactosidase antibody (Biotrend). These experiments also showed specific recruitment of the enzyme to the LoVo cells, whereas the HEK 293 cells were not stained. Control experiments with untransfected HEK 293 cells were negative. These experiments prove that the single-chain double antigen-binding protein specifically and selectively recognizes tumor cells.

In further experiments, conversion of nontoxic daunomycin β-D-galactopyranoside into the cytotoxic daunomycin was investigated. It was possible by incubating LoVo cells with purified single-chain double antigen-binding protein (10 μg/ml) for one hour and subsequent incubation with β-galactosidase (1 μg/ml) and daunomycin β-D-galactopyranoside (2 μM) at 37° for one hour to detect a specific localization of the resulting daunomycin in the nucleus by the autofluorescence of the substance, comparable to the staining due to direct incubation with daunomycin. No nuclear staining was detectable in the absence of single-chain double antigen-binding protein or β-galactosidase, and with control cells (HEK 293; HEK producing single-chain double antigen-binding protein). These experiments prove that the single-chain double antigen-binding protein is able to recruit an enzyme to a tumor cell, and that this enzyme can be employed to convert a nontoxic precursor into a toxic substance.

This effect can be used in further experiments to kill tumor cells specifically.

Figure 8A:
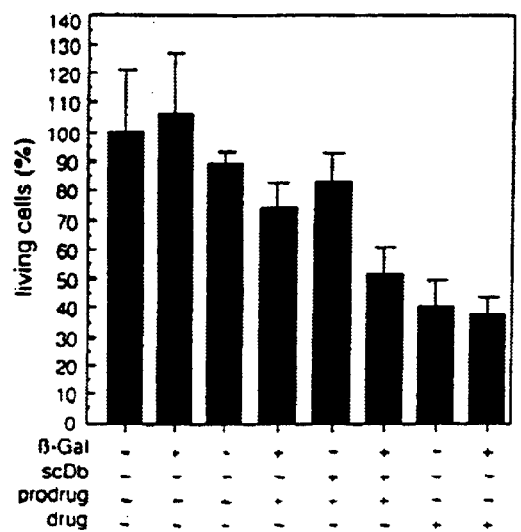
FIG. 8 A shows the death of LoVo cells in the presence of the single-chain double antigen-binding protein according to the invention (scDb), β-galactosidase (β-Gal), daunomycin β-D-galactopyranoside (prodrug) and/or daunomycin (drug).
Figure 8B:
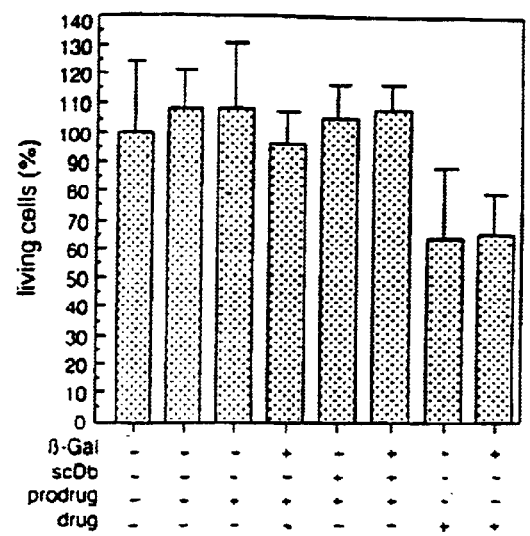

For this purpose, the LoVo cells were incubated in 96-well plates with a single-chain double antigen-binding protein (10 μg/ml) and then with daunomycin β-D-galactopyranoside (5 μM) at 37° C. for one hour. The death of the cells was analyzed after 2 days using a WST test (Boehringer Mannheim) (FIG. 8). In this case, the death of the cells on conversion of the prodrug into the drug was approximately as good as in the presence of the drug (FIG. 8A). Essentially no effect was found in the absence of one component or with CEA-negative A549 cells (FIG. 8B).

Example 4
Preparation of constructs for intracellular expression of single-chain double antigen-binding proteins For intracellular expression of the single-chain double antigen-binding protein, the DNA of the gene for the single-chain double antigen-binding protein is amplified with various primers:

transmembrane single-chain double antigen-binding protein (TM-scDAP). A primer which inserts the transmembrane domain of PDGFR at the 3' end of the gene is used for this (SEQ ID NO: 15)

(LPFKVVVISAIIALVVLTIISLIILIMLWQKKPRYES)

Single-chain double antigen-binding protein localized in the endoplasmatic reticulum (ER-scDAP). A primer which inserts an ER retention signal (SEKDEL) at the 3' end of the gene is used for this.

Single-chain double antigen-binding protein localized in the cytoplasm (cyto-scDAP). A primer which replaces the signal sequence at the 5' end of the gene by a methionine and a Kozak sequence for optimal translation initiation is used for this.

Single-chain double antigen-binding protein localized in the nucleus (nuc-scDb). Primers which replace the signal sequence at the 5' end of the gene by a methionine and a Kozak sequence for optimal translation initiation and insert a nuclear localization sequence at the 3' end of the gene (SEQ ID NO: 16) (P KKKRKVGGGT; the nuclear localization sequence is underlined) are used for this.

These fragments are cloned into suitable eukaryotic expression vectors (pSecTagA and pcDNA3; Invitrogen). The resulting constructs (TM-scDAP, ER-scDAP, cyto-scDAP, nuc-scDAP, and sec-scDAP (=secreted protein; see Example 2) are then transiently transfected into eukaryotic cells (3T3), and the localization of the expressed protein is investigated by immunofluorescence using an anti-Myc epitope antibody. A staining typical of the secretory pathway can be detected for the constructs sec-scDAP, ER-scDAP and TM-scDAP, whereas cyto-scDAP shows a diffuse localization in the cytoplasm and nuc-scDAP shows localization in the nucleus.

Priority applications, German patent application numbers, DE 198 16 14.7 and DE198 27 239.1, filed Apr. 9, 1998 and Jun. 18, 1998, respectively, including drawings, claims, and abstract, are incorporated herein by reference in their entirety.

What is claimed is:

1. A single-chain multiple antigen-binding molecule comprising:
   (a) a variable domain of a heavy chain of an immunoglobulin (VH) with a first specificity (A), or functional parts thereof, wherein the first specificity (A) is directed against the cell membrane of a target cell,
   (b) a variable domain of a light chain of an immunoglobulin (VL) with a second specificity (B), or functional parts thereof, wherein the second specificity (B) is directed against a vector selected from the group consisting of a nucleic acid and a viral vector selected from the group consisting of an AdV, AAV, Vaccinia, RSV, HSV, influenza, and lentivirus,
   (c) a variable domain of a heavy chain of an immunoglobulin (VH) with the specificity (B), or functional parts thereof, and
   (d) a variable domain of a light chain of an immunoglobulin (VL) with the specificity (A), or functional parts thereof,
wherein the VH and VL domains are connected in the form of a VH-VL construct or VL-VH construct, and wherein the two VH-VL constructs are connected via a peptide (P).

2. A single-chain multiple antigen-binding molecule as claimed in claim 1, which consists of two VH-VL constructs.

3. A single-chain multiple antigen-binding molecule as claimed in claim 1, wherein the VH-VL constructs are connected via domains with the same specificity.

4. A single-chain multiple antigen-binding molecule as claimed in claim 1, wherein the VH and VL domains are connected via a peptide linker (L) in the form of a VH-L-VL construct or VL-L-VH construct.

5. A single-chain multiple antigen-binding molecule as claimed in claim 4, wherein the linker (L) is about 1–20 amino acids long.

6. A single-chain multiple antigen-binding molecule as claimed in claim 5, wherein the linker (L) is about 1–5 amino acids long.

7. A single-chain multiple antigen-binding molecule as claimed in claim 6, wherein the linker (L) comprises the amino acid sequence GGGGS.

8. A single-chain multiple antigen-binding molecule as claimed in claim 1, wherein the peptide (P) is about 12–40 amino acids long.

9. A single-chain multiple antigen-binding molecule as claimed in claim 8, wherein the peptide (P) is about 12–20 amino acids long.

10. A single-chain multiple antigen-binding molecule as claimed in claim 9, wherein the peptide (P) is 14 amino acids long.

11. A single-chain multiple antigen-binding molecule as claimed in claim 8, wherein the peptide (P) comprises the amino acid sequence GGGGSGGRASGGGS (SEQ ID NO: 2) or GGGGSGGRASGGGGS (SEQ ID NO: 3).

12. A single-chain multiple antigen-binding molecule as claimed in claim 11, wherein the peptide (P) has an amino acid sequence selected from the group consisting of GGGGSGGRASGGGS (SEQ ID NO: 2) and GGGGSGRASGGGGS (SEQ ID NO: 3).

13. A single-chain multiple antigen-binding molecule as claimed in claim 1, wherein said molecule further comprises an effector (E) which effector (E) is a prodrug activating enzyme.

14. A single-chain multiple antigen-binding molecule as claimed in claim 13, wherein the effector (E) is linked to said molecule via a connector (B).

15. A single-chain multiple antigen-binding molecule as claimed in claim 14, wherein the connector (B) comprises a protease cleavage sequence.

16. A single-chain multiple antigen-binding molecule as claimed in claim 15, wherein the protease cleavage sequence is selected from the group consisting of PSA, cathepsin, plasminogen and plasminogen activator cleavage sequence.

17. A single-chain multiple antigen-binding molecule as claimed in claim 1, wherein the peptide (P) further comprises a fusogenic peptide.

18. A single-chain multiple antigen-binding molecule as claimed in claim 1, wherein the cell membrane is selected from the group consisting of cell membrane of lymphocytes, macrophages, monocytes, granulocytes, hematopoietic cells, endothelial cells, smooth muscle cells, striped muscle cells, epithelial cells, liver cells, kidney cells, glia cells, cells of the supporting tissue, tumor cells and leukemia cells.

19. A single-chain multiple antigen-binding molecule as claimed in claim 1, wherein the first specificity (A) is directed against a protein.

* * * * *

SEQUENCE LISTING

```
<160> NUMBER OF SEQ ID NOS: 40

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide

<400> SEQUENCE: 1

Gly Gly Gly Gly Ser
1               5

<210> SEQ ID NO 2
<211> LENGTH: 14
<212> TYPE: PRT
<213> ORGANISM: Artificial Sequence
<220> FEATURE:
<223> OTHER INFORMATION: Synthetic peptide

<400> SEQUENCE: 2

Gly Gly Gly Gly Ser Gly Gly Arg Ala Ser Gly Gly Gly Ser
1               5                   10

<210> SEQ ID NO 3
<211> LENGTH: 15
<212> TYPE: PRT
<213> ORGANISM: Artificial Sequence
<220> FEATURE:
<223> OTHER INFORMATION: Synthetic peptide

<400> SEQUENCE: 3

Gly Gly Gly Gly Ser Gly Gly Arg Ala Ser Gly Gly Gly Gly Ser
1               5                   10                  15

<210> SEQ ID NO 4
<211> LENGTH: 26
<212> TYPE: DNA
<213> ORGANISM: Artificial Sequence
<220> FEATURE:
<223> OTHER INFORMATION: Synthetic nucleotide

<400> SEQUENCE: 4
ggaagcagac cacgtggtct gcttcc                                          26

<210> SEQ ID NO 5
<211> LENGTH: 68
<212> TYPE: DNA
<213> ORGANISM: Artificial Sequence
<220> FEATURE:
<223> OTHER INFORMATION: Synthetic nucleotide

<400> SEQUENCE: 5
```

```
agcaggtgtt gggaggcagc aggtgttggg aggcagcagg tgttgggagg cagcaggtgt    60
tgggaggc                                                             68

<210> SEQ ID NO 6
<211> LENGTH: 41
<212> TYPE: DNA
<213> ORGANISM: Artificial Sequence
<220> FEATURE:
<223> OTHER INFORMATION: Synthetic nucleotide

<400> SEQUENCE: 6
ggccgatggg cagatagagg gggccgatgg gcagatagag g                        41

<210> SEQ ID NO 7
<211> LENGTH: 26
<212> TYPE: DNA
<213> ORGANISM: Artificial Sequence
<220> FEATURE:
<223> OTHER INFORMATION: Synthetic nucleotide

<400> SEQUENCE: 7
ggaagcagac cagctggtct gcttcc                                         26

<210> SEQ ID NO 8
<211> LENGTH: 11
<212> TYPE: PRT
<213> ORGANISM: Artificial Sequence
<220> FEATURE:
<223> OTHER INFORMATION: Synthetic peptide

<400> SEQUENCE: 8

Glu Gln Lys Leu Ile Ser Glu Glu Asp Leu Asn
1               5                   10

<210> SEQ ID NO 9
<211> LENGTH: 6
<212> TYPE: PRT
<213> ORGANISM: Artificial Sequence
<220> FEATURE:
<223> OTHER INFORMATION: Synthetic peptide

<400> SEQUENCE: 9

His His His His His His
1               5

<210> SEQ ID NO 10
<211> LENGTH: 45
<212> TYPE: DNA
<213> ORGANISM: Artificial Sequence
<220> FEATURE:
<223> OTHER INFORMATION: Primer

<400> SEQUENCE: 10
ttgttctgcg gccgcccgtt tcagctccag cttggtgcca gcacc                    45

<210> SEQ ID NO 11
<211> LENGTH: 59
<212> TYPE: DNA
<213> ORGANISM: Artificial Sequence
<220> FEATURE:
<223> OTHER INFORMATION: Primer

<400> SEQUENCE: 11
tgcatgctag ggcgcgcctc gggcggaggt ggctcacagg tgcagctggt gcaatctgg     59
```

<210> SEQ ID NO 12
<211> LENGTH: 60
<212> TYPE: DNA
<213> ORGANISM: Artificial Sequence
<220> FEATURE:
<223> OTHER INFORMATION: Primer

<400> SEQUENCE: 12
gctcggtaag gcgcgcccac cgctgccacc gcctccacct aggacggtca gcttggtccc    60

<210> SEQ ID NO 13
<211> LENGTH: 32
<212> TYPE: DNA
<213> ORGANISM: Artificial Sequence
<220> FEATURE:
<223> OTHER INFORMATION: Primer

<400> SEQUENCE: 13
ttactcgcgg cccagccggc cacggcccag gt                                  32

<210> SEQ ID NO 14
<211> LENGTH: 7
<212> TYPE: PRT
<213> ORGANISM: Artificial Sequence
<220> FEATURE:
<223> OTHER INFORMATION: Synthetic peptide

<400> SEQUENCE: 14

Ala Ala Gln Pro Ala Thr Ala
1               5

<210> SEQ ID NO 15
<211> LENGTH: 37
<212> TYPE: PRT
<213> ORGANISM: Artificial Sequence
<220> FEATURE:
<223> OTHER INFORMATION: Synthetic peptide

<400> SEQUENCE: 15

Leu Pro Phe Lys Val Val Ile Ser Ala Ile Ile Ala Leu Val Val
1               5                   10                  15

Leu Thr Ile Ile Ser Leu Ile Ile Leu Ile Met Leu Trp Gln Lys Lys
            20                  25                  30

Pro Arg Tyr Glu Ser
        35

<210> SEQ ID NO 16
<211> LENGTH: 11
<212> TYPE: PRT
<213> ORGANISM: Artificial Sequence
<220> FEATURE:
<223> OTHER INFORMATION: Synthetic peptide

<400> SEQUENCE: 16

Pro Lys Lys Lys Arg Lys Val Gly Gly Gly Thr
1               5                   10

<210> SEQ ID NO 17
<211> LENGTH: 6
<212> TYPE: DNA
<213> ORGANISM: Artificial Sequence
<220> FEATURE:
<223> OTHER INFORMATION: Synthetic nucleotide

<400> SEQUENCE: 17

-continued

```
gccacc                                                              6

<210> SEQ ID NO 18
<211> LENGTH: 6
<212> TYPE: DNA
<213> ORGANISM: Artificial Sequence
<220> FEATURE:
<223> OTHER INFORMATION: Synthetic nucleotide

<400> SEQUENCE: 18 gccgcc                                                              6

<210> SEQ ID NO 19
<211> LENGTH: 4
<212> TYPE: PRT
<213> ORGANISM: Artificial Sequence
<220> FEATURE:
<223> OTHER INFORMATION: Synthetic peptide

<400> SEQUENCE: 19

Gly Gly Gly Ser
1

<210> SEQ ID NO 20
<211> LENGTH: 20
<212> TYPE: PRT
<213> ORGANISM: Artificial Sequence
<220> FEATURE:
<223> OTHER INFORMATION: Synthetic peptide

<400> SEQUENCE: 20

Gly Leu Phe Glu Ala Leu Leu Glu Leu Leu Glu Ser Leu Trp Glu Leu
1               5                   10                  15

Leu Leu Glu Ala
            20

<210> SEQ ID NO 21
<211> LENGTH: 28
<212> TYPE: PRT
<213> ORGANISM: Artificial Sequence
<220> FEATURE:
<223> OTHER INFORMATION: Synthetic peptide

<400> SEQUENCE: 21

Ala Ala Leu Ala Glu Ala Leu Ala Glu Ala Leu Ala Glu Ala Leu Ala
1               5                   10                  15

Glu Ala Leu Ala Glu Ala Leu Ala Ala Ala Gly Cys
            20                  25

<210> SEQ ID NO 22
<211> LENGTH: 19
<212> TYPE: PRT
<213> ORGANISM: Artificial Sequence
<220> FEATURE:
<223> OTHER INFORMATION: Synthetic peptide

<400> SEQUENCE: 22

Phe Ala Gly Val Val Leu Ala Gly Ala Ala Leu Gly Val Ala Ala Ala
1               5                   10                  15

Ala Gln Ile

<210> SEQ ID NO 23
<211> LENGTH: 20
<212> TYPE: PRT
<213> ORGANISM: Artificial Sequence
```

```
<220> FEATURE:
<223> OTHER INFORMATION: Synthetic peptide

<400> SEQUENCE: 23

Gly Leu Phe Gly Ala Ile Ala Gly Phe Ile Glu Gly Gly Trp Trp Gly
1               5                   10                  15

Met Ile Asp Gly
            20

<210> SEQ ID NO 24
<211> LENGTH: 40
<212> TYPE: PRT
<213> ORGANISM: Artificial Sequence
<220> FEATURE:
<223> OTHER INFORMATION: Synthetic peptide

<400> SEQUENCE: 24

Gly Leu Phe Gly Ala Ile Ala Gly Phe Ile Glu Asn Gly Trp Glu Gly
1               5                   10                  15

Met Ile Asp Gly Gly Leu Phe Gly Ala Ile Ala Gly Phe Ile Glu Asn
            20                  25                  30

Gly Trp Glu Gly Met Ile Asp Gly
        35                  40

<210> SEQ ID NO 25
<211> LENGTH: 11
<212> TYPE: PRT
<213> ORGANISM: Artificial Sequence
<220> FEATURE:
<223> OTHER INFORMATION: Synthetic peptide

<400> SEQUENCE: 25

Gly Leu Phe Gly Ala Ile Ala Gly Phe Ile Glu
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Synthetic peptide

<400> SEQUENCE: 26

Ala Leu Phe Gly Ala Ile Ala Gly Phe Ile Glu
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Synthetic peptide

<400> SEQUENCE: 27

Leu Phe Leu Gly Ala Ile Ala Gly Phe Ile Glu
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Synthetic peptide

<400> SEQUENCE: 28
```

Leu Leu Leu Gly Ala Ile Ala Gly Phe Ile Glu
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Synthetic peptide

<400> SEQUENCE: 29

Leu Ile Leu Gly Ala Ile Ala Gly Phe Ile Glu
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Synthetic peptide

<400> SEQUENCE: 30

Gly Ile Phe Gly Ala Ile Ala Gly Phe Ile Glu
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Synthetic peptide

<400> SEQUENCE: 31

Gly Leu Leu Gly Ala Ile Ala Gly Phe Ile Glu
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic peptide

<400> SEQUENCE: 32

Gly Leu Phe Ala Ala Ile Ala Gly Phe Ile Glu
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Synthetic peptide

<400> SEQUENCE: 33

Gly Leu Phe Glu Ala Ile Ala Gly Phe Ile Glu
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Synthetic peptide

<400> SEQUENCE: 34

Gly Leu Phe Gly Ala Met Ala Gly Phe Ile Glu

```
1               5                  10

<210> SEQ ID NO 35
<211> LENGTH: 11
<212> TYPE: PRT
<213> ORGANISM: Artificial Sequence
<220> FEATURE:
<223> OTHER INFORMATION: Synthetic peptide

<400> SEQUENCE: 35

Gly Leu Phe Gly Ala Ile Ala Gly Leu Ile Glu
1               5                  10

<210> SEQ ID NO 36
<211> LENGTH: 11
<212> TYPE: PRT
<213> ORGANISM: Artificial Sequence
<220> FEATURE:
<223> OTHER INFORMATION: Synthetic peptide

<400> SEQUENCE: 36

Gly Leu Phe Gly Ala Ile Ala Gly Phe Ile Val
1               5                  10

<210> SEQ ID NO 37
<211> LENGTH: 20
<212> TYPE: PRT
<213> ORGANISM: Artificial Sequence
<220> FEATURE:
<223> OTHER INFORMATION: Synthetic peptide

<400> SEQUENCE: 37

Gly Leu Phe Glu Ala Ile Ala Glu Phe Ile Glu Gly Gly Trp Glu Gly
1               5                  10                  15

Leu Ile Glu Gly
            20

<210> SEQ ID NO 38
<211> LENGTH: 20
<212> TYPE: PRT
<213> ORGANISM: Artificial Sequence
<220> FEATURE:
<223> OTHER INFORMATION: Synthetic peptide

<400> SEQUENCE: 38

Gly Leu Leu Glu Ala Leu Ala Glu Leu Leu Glu Gly Gly Trp Glu Gly
1               5                  10                  15

Leu Leu Glu Gly
            20

<210> SEQ ID NO 39
<211> LENGTH: 5
<212> TYPE: PRT
<213> ORGANISM: Artificial Sequence
<220> FEATURE:
<223> OTHER INFORMATION: Synthetic peptide

<400> SEQUENCE: 39

Pro Asp Gly Phe Arg
1               5

<210> SEQ ID NO 40
<211> LENGTH: 6
<212> TYPE: PRT
<213> ORGANISM: Artificial Sequence
<220> FEATURE:
```

-continued

<223> OTHER INFORMATION: Synthetic peptide

<400> SEQUENCE: 40

Ser Glu Lys Asp Glu Leu
1               5